United States Patent
Ozaki et al.

(10) Patent No.: US 11,478,482 B2
(45) Date of Patent: *Oct. 25, 2022

(54) FASUDIL FOR THE TREATMENT OF SCHIZOPHRENIA

(71) Applicant: NATIONAL UNIVERSITY CORPORATION TOKAI NATIONAL HIGHER EDUCATION AND RESEARCH SYSTEM, Nagoya (JP)

(72) Inventors: Norio Ozaki, Nagoya (JP); Kiyofumi Yamada, Nagoya (JP); Taku Nagai, Nagoya (JP); Daisuke Mori, Nagoya (JP); Yuko Arioka, Nagoya (JP); Itaru Kushima, Nagoya (JP)

(73) Assignee: NATIONAL UNIVERSITY CORPORATION TOKAI NATIONAL HIG, Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/588,822

(22) Filed: Jan. 31, 2022

(65) Prior Publication Data

US 2022/0152040 A1   May 19, 2022

Related U.S. Application Data

(63) Continuation of application No. 17/284,824, filed as application No. PCT/JP2019/035488 on Sep. 10, 2019.

(30) Foreign Application Priority Data

Oct. 15, 2018  (JP) .................. 2018-194682

(51) Int. Cl.
| C07D 217/02 | (2006.01) |
| A61K 31/551 | (2006.01) |
| A61P 25/18 | (2006.01) |

(52) U.S. Cl.
CPC ............ A61K 31/551 (2013.01); A61P 25/18 (2018.01)

(58) Field of Classification Search
CPC .................................................. C07D 217/02

USPC ........................................................ 546/139
See application file for complete search history.

(56) References Cited

U.S. PATENT DOCUMENTS

2011/0237600 A1    9/2011  Nikolich et al.

FOREIGN PATENT DOCUMENTS

JP          2011/519972 A      7/2011

OTHER PUBLICATIONS

International Search Report of International Application No. PCT/JP2019/035488, dated Nov. 26, 2019.
Garcia-Rojo, Gonzalo et al., "The ROCK Inhibitor Fasudil Prevents Chronic Restraint Stress-Induced Depressive-Like Behaviors and Dendritic Spine Loss in Rat Hippocampus", International Journal of Neuropsychopharmacology, 2017, pp. 336-345, vol. 20, No. 4.
Meziane, Hamid et al., "Fasudil treatment in adult reverses behavioural changes and brain ventricular enlargement in Oligophrenin-1 mouse model of intellectual disability", Human Molecular Genetics, 2016, pp. 2314-2323, vol. 25, No. 11.
Wrobel, Andrzej et al., "Inhibition of Rho kinase by GSK 269962 reverses both corticosterone-induced detrusor overacti vi ty and depression-like behaviour in rats", European Journal of Pharmacology, Aug. 30, 2018, pp. 127-136, vol. 837.
Inan, Salim Yalcin et al., "Infralimbic cortex Rho-kinase inhibition causes antidepressant-like activity in rats", Progress n Neuro-Psychopharmacology & Biological Psychiatry, Mar. 3, 2015, pp. 36-43, vol. 57.
Li, Li et al., "Selective targeting of M-type potassium Kv7.4 channels demonstrates their key role in the regulation of dopaminergic neuronal excitability and depression-like behaviour", British Journal of Pharmacology, Dec. 2017, pp. 4277-4294, vol. 174, No. 23.
Swanger, Sharon A. et al., "ROCKI and ROCK2 inhibition alters dendritic spine morphology in hippocampal neurons", Cellular Logistics, 2015, vol. 5, No. 4, article No. e1133266.
Kushima et al., "High-resolution copy number variation analysis of schizophrenia in Japan", Molecular Psychiatry, 2017, pp. 430-440, vol. 22.

*Primary Examiner* — Douglas M Willis
(74) *Attorney, Agent, or Firm* — McBee Moore & Vanik IP, LLC

(57) ABSTRACT

The present invention provides an antipsychotic drug comprising fasudil or a pharmaceutically acceptable salt thereof as an active agent for the treatment of schizophrenia, including schizophrenia caused by dysfunction of ARHGAP10.

17 Claims, 7 Drawing Sheets

A

B

**p<0.01

A

B $*p<0.05, **p<0.01$

FASUDIL FOR THE TREATMENT OF SCHIZOPHRENIA

CROSS REFERENCE TO RELATED APPLICATIONS

This application is a Continuation of U.S. patent application Ser. No. 17/284,824, filed 13 Apr. 2021, which is the U.S. National Stage Application of PCT/JP2019/035488 filed 10 Sep. 2019, which claims priority to Japanese Patent Application No. 2018-194682 filed on Oct. 15, 2018, each of these applications are incorporated herein by reference in its entirety.

TECHNICAL FIELD

The present invention relates to an antipsychotic drug (a therapeutic agent for a mental disorder). More specifically, the present invention relates to a therapeutic agent for a mental disorder with abnormal neurodevelopment as a pathological condition, and its applications, etc.

BACKGROUND ART

Schizophrenia is a mental disorder that shows positive symptoms such as hallucination-delusion, negative symptoms characterized by poor speech and facial expression and lack of motivation, and cognitive dysfunction in memory and concentration, etc. The prevalence of schizophrenia is about 1% of the general population. In Japan alone, about 700,000 patients with schizophrenia are undergoing treatment, but there are many intractable cases for which current treatment is not sufficiently effective. As a result, 153,000 of the patients in treatment are forced to be hospitalized in psychiatric beds (2017). In addition, the life expectancy of schizophrenic patients is 10 to 25 years shorter than for the general population. Taking the above into consideration, the economic loss caused by schizophrenia in Japan is calculated to be 2.8 trillion yen every year (2013).

Since cardiovascular disease is a common cause of early death in schizophrenia, molecules involved in both the brain and the heart are assumed to play a role in the pathological condition of schizophrenia. The development of a therapeutic agent with excellent effects and fewer side effects on the cardiovascular system or the like is long awaited. However, the details of the pathology of schizophrenia are still unknown, and the development of pathology-based treatment agents has not progressed.

Although the pathology of schizophrenia is still unknown, epidemiological studies have shown that the involvement of genetic factors in its onset is higher than in other mental disorders. A research group of the present inventors conducted genomic copy number variation (CNV) analysis in Japanese schizophrenia patients and identified rare CNVs involved in the onset of schizophrenia in 9% of all patients (Non-patent Literature (NPL) 1). As a result of further analysis, the present inventors identified CNVs in the ARHGAP10 gene, which belongs to the RhoGAP family associated with neurodevelopment and cardiovascular function, in five patients (four deletions and one duplication) and found that the CNVs are statistically associated with the onset of schizophrenia. One of the patients with a deletion in the ARHGAP10 gene had a single nucleotide variant (SNV) that causes an amino acid substitution (Ser490→Pro) in the RhoGAP domains of alleles simultaneously (FIG. 1A).

ARHGAP10 protein is a GTPase-activating protein that has the function of inactivating low-molecular-weight G proteins, such as RhoA and Cdc42, is widely distributed in the body, including the brain and cardiac muscle, and plays an important role in the regulation of various physiological functions, such as actin cytoskeleton regulation through the regulation of the activity of effector Rho kinase or the like. It is suggested that an decrease of the ARHGAP10 expression level due to deletion of the ARHGAP10 gene increases active forms of RhoA and Cdc42 in cells, thus increasing the activity of Rho kinase. The present inventors examined the influence of SNV in the RhoGAP domain identified in one schizophrenic patient in an in vitro binding experiment. As a result, the inventors found that the SNV mutant lost its ability to bind to RhoA and clarified that the ARHGAP10 SNV mutant cannot inactivate RhoA as a substrate (FIG. 1B).

CITATION LIST

Non-Patent Literature (NPL)

NPL 1: Kushima I. et al., High-resolution copy number variation analysis of schizophrenia in Japan. Mol Psychiatry 22: 430-440, 2017

SUMMARY OF INVENTION

Technical Problem

In view of the above background, an object of the present invention is to provide a novel therapeutic agent for mental disorders with abnormal neurodevelopment as a pathological condition, such as schizophrenia.

Solution to Problem

The present inventors conducted further research to develop a novel therapeutic agent based on the pathology of schizophrenia. As a result of detailed experiments using model mice and dopaminergic neurons derived from patient-derived iPS cells, it was shown that Rho kinase inhibitors exhibit excellent antipsychotic effects and are useful as a novel therapeutic agent based on the pathology of schizophrenia. On the other hand, as a result of considering experimental results as well as known genomic variations associated with various mental disorders and the scope of application of existing schizophrenia drugs (e.g., the fact that schizophrenia drugs are also applied to other mental disorders, such as bipolar disorder), Rho kinase inhibitors were reasonably expected to be useful as a novel therapeutic agent for various mental disorders with abnormal neurodevelopment as a pathological condition (e.g., schizophrenia, autism spectrum disorder, bipolar disorder, and depression).

The following inventions are based on the above results and considerations.

[1] An antipsychotic drug comprising a Rho kinase inhibitor or a pharmacologically acceptable salt thereof as an active ingredient.

[2] The antipsychotic drug according to [1], which normalizes dysfunction of ARHGAP10.

[3] The antipsychotic drug according to [1] or [2], wherein the Rho kinase inhibitor is fasudil or ripasudil.

[4] The antipsychotic drug according to any one of [1] to [3], which is for use in the treatment of a mental disorder with abnormal neurodevelopment as a pathological condition.

[5] The antipsychotic drug according to [4], wherein the mental disorder is caused by dysfunction of ARHGAP10.
[6] The antipsychotic drug according to [4] or [5], wherein the mental disorder is schizophrenia, autism spectrum disorder, bipolar disorder, or depression.
[7] A method for treating a mental disorder with abnormal neurodevelopment as a pathological condition, the method comprising the step of administering a therapeutically effective amount of a Rho kinase inhibitor to a patient in need of treatment or prevention.
[8] The therapeutic method according to [7], wherein the mental disorder is caused by dysfunction of ARHGAP10.
[9] The therapeutic method according to [7] or [8], wherein the mental disorder is schizophrenia, autism spectrum disorder, bipolar disorder, or depression.

DESCRIPTION OF EMBODIMENTS

Figure 1:
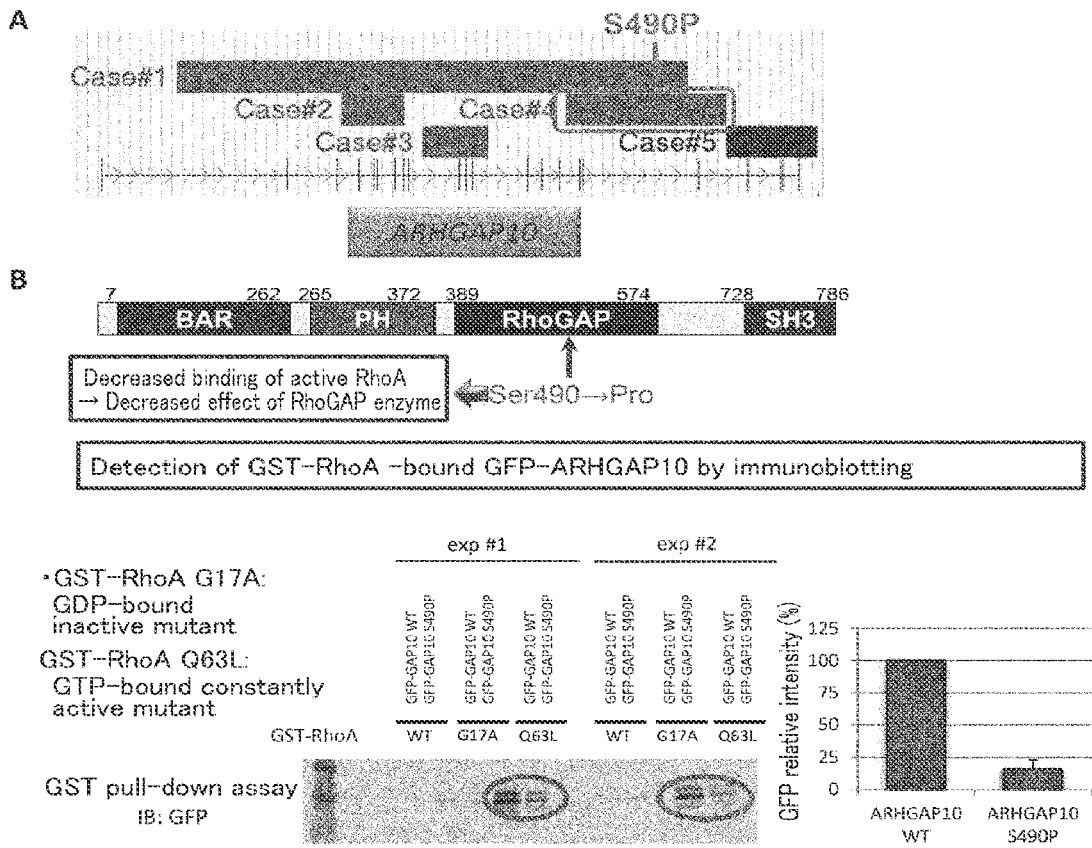
FIG. 1 shows a single nucleotide polymorphism of ARHGAP10 identified in a patient (Ser490→Pro) (A) and its effect (B). The ARHGAP10 SNV mutant had reduced binding ability to RhoA.

A first aspect of the present invention relates to an antipsychotic drug. The term "antipsychotic drug" refers to a pharmaceutical agent that has a therapeutic or prophylactic effect on mental disease or mental disorder. Therapeutic effects include, for example, alleviating (ameliorating) conditions characteristic of mental disease/mental disorder or accompanying symptoms, and preventing or delaying the worsening of symptoms. The latter can be regarded as a prophylactic effect because it prevents aggravation of illness. Thus, therapeutic effects and prophylactic effects are partially overlapping concepts; it is difficult to clearly distinguish one from the other, and there is little benefit in doing so. A typical prophylactic effect is to prevent or delay the recurrence (onset) of symptoms that are characteristic of a mental disease or mental disorder. As long as a drug (a substance) has some therapeutic or prophylactic effect, or both effects, on a mental disease or mental disorder, the drug (the substance) is categorized as an antipsychotic drug.

The antipsychotic drug of the present invention contains a Rho kinase inhibitor as an active ingredient. Rho kinase inhibitors selectively inhibit Rho kinase (ROCK), which is one of the protein phosphatases. Rho kinase, which is serine/tyrosine kinase, is a target of the low-molecular-weight GTP-binding protein Rho and is involved in various cellular functions. Examples of Rho kinase inhibitors include fasudil, hydroxyfasudil, ripasudil, netarsudil, thiazovivin, (1-benzylpyrrolidin-3-yl)-(1H-indazol-5-yl)amine, (1-benzylpiperidin-4-yl)-(1H-indazol-5-yl)amine, N-[2-(4-fluorophenyl)-6,7-dimethoxy-4-kinazolinyl]-N-(1H-indazol-5-yl)amine, N-4-(1H-indazol-5-yl)-6,7-dimethoxy-N-2-pyridin-4-yl-quinazoline-2,4-diamine, 4-methyl-5-(2-methyl-[1,4]diazepan-1-sulfonyl)isoquinolin, Y-27632 ((R)-(+)-trans-N-(4-pyridyl)-4-(1-aminoethyl)-cyclohexanecarboxamide), RKI 1447 (N-[(3-hydroxyphenyl)methyl]-N'-[4-(4-pyridinyl)-2-thiazolyl] urea), GSK429286A (N)-(6-fluoro-1H-indazol-5-yl)-1,4,5,6-tetrahydro-2-methyl-6-oxo-4-[4-(trifluoromethyl)phenyl]-3-pyridinecarboxamide), Y-30141(4-(1-aminoethyl)-N-(1H-pyrrolo(2,3-b)pyridin-4-yl) cyclohexanecarboxamide), and Y-39983 (4-[(1R)-1-aminoethyl]-N-1H-pyrrolo[2,3-b]pyridin-4-ylbenzamide dihydrochloride). In the present invention, fasudil and ripasudil are particularly preferable Rho kinase inhibitors. A pharmaceutical preparation containing fasudil hydrochloride hydrate (hexahydro-1-(5-isoquinolinesulfonyl)-1H-1,4-diazepine monohydrochloride hemihydrate) as an active ingredient (Elill, registered trademark) is applied to improve cerebral vasospasm and associated cerebral ischemic symptoms after subarachnoid hemorrhage surgery vasoconstriction, whereas a pharmaceutical preparation containing lipasudil hydrochloride hydrate (4-fluoro-5-{[(2S)-2-methyl-1,4-diazepan-1-yl]sulfonyl}isoquinoline monohydrochloride dihydrate) as an active ingredient (Granatek (registered trademark)) is applied to the treatment of glaucoma and ocular hypertension.

The active ingredients of the antipsychotic drugs of the present invention can take various forms, such as salts, hydrates, and solvates, as long as they are pharmacologically acceptable. For example, various salts, such as salts with inorganic bases, salts with organic bases, salts with inorganic acids, salts with organic acids, salts with basic amino acids, and salts with acidic amino acids, can be used. Examples of salts with inorganic bases include alkali metal salts (e.g., sodium salts, potassium salts, etc.), alkaline earth metal salts (e.g., calcium salts, magnesium salts, etc.), aluminum salts, and ammonium salts. Examples of salts with organic bases include salts with trimethylamine, triethylamine, pyridine, picoline, ethanolamine, diethanolamine, triethanolamine, dicyclohexylamine, and N,N'-dibenzylethylenediamine. Examples of salts with inorganic acids include salts with hydrochloric acid, hydrobromic acid, nitric acid, sulfuric acid, phosphoric acid, and the like. Examples of salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like. Examples of salts with basic amino acids include salts with arginine, lysine, ornithine, and the like. Examples of salts with acidic amino acids include salts with aspartic acid, glutamic acid, and the like. These salts can be prepared by conventional means. The above examples should not be used for limited interpretation of "pharmacologically acceptable salts." That is, "pharmacologically acceptable salt" should be interpreted in a broad sense and is a term that includes various salts.

The active ingredient of the antipsychotic drug of the present invention may be in the form of a prodrug. A "prodrug" is a compound in a form that is inactive or has low activity, and that is converted to an active substance and exhibits pharmaceutical efficacy when administered to a living body. For example, prodrugs are used for the purpose of improving bioavailability and reducing side effects. Examples of prodrugs include compounds obtained by subjecting an amino, sulfide, or like group of an original pharmaceutical active substance to sulfonylation, acylation, alkylation, phosphorylation, boration, carbonation, esterification, amidation, urethanization, etc.

The antipsychotic drug of the present invention can also be used in combination with one or more other antipsychotic drugs that have a mechanism of action different from that of the Rho kinase inhibitor (referred to below as "other active ingredients"). The number of other active ingredients may be two or more. Examples of other active ingredients include aripiprazole, asenapine, olanzapine, quetiapine, clozapine, paliperidone, perospirone, blonanserin, risperidone, chlorpromazine, levomepromazine, perphenazine, fluphenazine, propericiazine, haloperidol, bromperidol, spiperone, moperone, pimozide, sulpiride, sultopride, tiapride, nemonapride, carpipramine, clocapramine, mosapramine, and zolpidem.

The form for combined use is not limited. Examples include a combination drug in which active ingredients are mixed together and a kit comprising a first component containing a Rho kinase inhibitor and a second component containing one or more other active ingredients (when two or more other active ingredients are used, various modes can be used, which include for example, a mode in which all of the other active ingredients can be combined into a second component, and a mode in which the two or more other active ingredients constitute individual components). When a kit is used, each component is administered at least once during the treatment period. The administration schedule for each component can be individually set. It is also possible to administer both components simultaneously. "Simultaneously" as referred to herein does not require strict simultaneity. Accordingly, the concept of simultaneity includes not only cases in which the both components are administered under conditions in which there is no time difference in their administration, such as when both components are mixed and then administered to the target, but also cases in which both components are administered under conditions in which there is no substantial time difference in their administration, such as when one component is first administered and then the other is administered immediately after the first administration.

Not to be confined to theory, but in view of the experimental results described below (in the Examples section), the antipsychotic drug of the present invention can provide its pharmaceutical efficacy (through normalization of dysfunction of ARHGAP10). Therefore, typically, mental disorders caused by dysfunction of ARHGAP10 (in other words, mental disorders caused by mutation in the ARHGAP10 gene) are targets of the treatment or prevention by the antipsychotic drug of the present invention (referred to below as "target disorder"). The target disorder is preferably a mental disorder with abnormal neurodevelopment as a pathological condition. Examples of mental disorders with abnormal neurodevelopment as a pathological condition include schizophrenia, autism spectrum disorder, bipolar disorder, and depression.

The antipsychotic drug of the present invention can be formulated according to usual methods. When the antipsychotic drug is formulated, other pharmaceutically acceptable components (e.g., carriers, excipients, disintegrants, buffers, emulsifiers, suspending agents, soothing agents, stabilizers, preservatives, antiseptics, surfactants, lubricants, diluents, coating agents, sugar coating agents, taste and odor masking agents, emulsifiers, solubilizers, dispersants, pH-adjusting agents, isotonic agents, solubilizing agents, flavors, coloring agents, dissolution aids, and saline) can be included. Examples of excipients that can be used include lactose, starch, sorbitol, D-mannitol, white sugar, and the like. Examples of disintegrants that can be used include starch, carboxymethyl cellulose, calcium carbonate, and the like. Examples of buffers that can be used include phosphates, citrates, acetates, and the like. Examples of emulsifiers that can be used include gum arabic, sodium alginate, tragacanth, and the like. Examples of suspending agents that can be used include glyceryl monostearate, aluminum monostearate, methyl cellulose, carboxymethyl cellulose, hydroxymethyl cellulose, sodium lauryl sulfate, and the like. Examples of soothing agents that can be used include benzyl alcohol, chlorobutanol, sorbitol, and the like. Examples of stabilizers that can be used include propylene glycol, ascorbic acid, and the like. Examples of preservatives that can be used include phenol, benzalkonium chloride, benzyl alcohol, chlorobutanol, methylparaben, and the like. Examples of antiseptic agents that can be used include benzalkonium chloride, p-hydroxybenzoate, chlorobutanol, and the like.

There are no limitations on the dosage form used in formulation. Examples of usable dosage forms include tablets, powders, fine granules, granules, capsules, syrups, liquids, suspensions, emulsions, jellies, injections, external preparations, inhalants, nasal drops, eye drops, and suppositories. The antipsychotic drug of the present invention contains the active ingredient in an amount necessary to achieve the expected therapeutic (or preventive) effect (i.e., a therapeutically effective amount). The amount of active ingredient in the antipsychotic drug of the present invention generally varies according to the dosage form, but the amount of active ingredient is set within the range of, for example, about 0.01% to 95% by weight so that the desired dose can be achieved.

The antipsychotic drug of the present invention is applied to the subject by oral or parenteral administration (e.g., through an intravenous, intra-arterial, subcutaneous, intramuscular, or intraperitoneal injection; or transdermal, intranasal, transmucosal, or like administration) depending on its dosage form. These routes of administration are not mutually exclusive, and two or more of any routes selected can be used in combination (for example, an intravenous injection can be performed simultaneously or at a specific time after the oral administration). Instead of systemic administration, local administration can also be used. The administration can also be performed using a drug delivery system (DDS) so that the active ingredient is delivered specifically to the target tissue.

A further aspect of the present invention is a method for treating a mental disease or mental disorder using the antipsychotic drug of the present invention (the concept of therapeutic method includes prophylactic treatment). The therapeutic method of the present invention includes the step of administering the antipsychotic drug of the present invention to a patient in need of treatment or prevention. The "patient in need of treatment or prevention" includes, for example, a person who is diagnosed as having, or is suspected of having, a mental disease or mental disorder (target disorder) that is the target of treatment or prevention; a person who presents characteristic pathological conditions or symptoms or shows signs of pathological conditions or symptoms; a person who shows signs of relapse; and the like. The dose of antipsychotics generally varies depending on the patient's symptoms, age, gender, weight, etc. However, a person skilled in the art would be able to set an appropriate dose. For example, an administration schedule of once to several times a day, once every two days, or once every three days can be used. When the administration schedule is set, the patient's symptoms and the duration of effect of the active ingredient can be taken into consideration.

EXAMPLES

1. Background and Purpose

Figure 2:
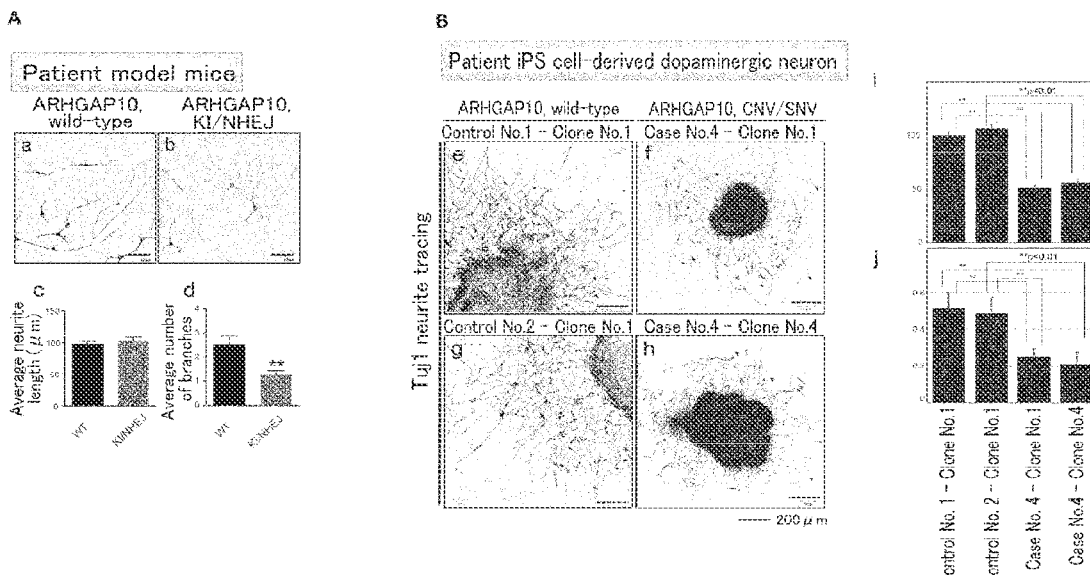
FIG. 2 shows morphological abnormality in patient-type ARHGAP10 mutant mouse neurons (A) and patient iPS cell-derived neurons (B). The length of neurites and the number of branches decreased in neurons of the primary culture of patient-type ARHGAP10 mutant mice (KI/NHEJ). In ARHGAP10 mutant patient (case No. 4) iPS cell-derived dopamine neurons, the length of neurites and the number of branches were reduced as compared with those in healthy subjects (the control).

In order to clarify the pathophysiological significance of ARHGAP10 gene mutation based on genetic-statistical and biochemical findings as well as previous reports and research results (see the Background Art section), the present inventors newly created genetically modified mice by genome editing technology using the genotype of a patient who had both ARHGAP10 deletion and SNV as a model. Behavioral analysis of the ARHGAP10-deficient/SNV model mice showed that the mice had a schizophrenia-like phenotype. In vitro morphological analysis of cultured neurons showed a reduction in neurite branching of the cultured neurons and a tendency toward immature neurodevelopment (FIG. 2, panel A). The results of the phenotypic analysis using the animal models also strongly suggested the possibility that the ARHGAP10 gene is associated with the onset of schizophrenia.

In addition, using iPS cells established from a patient with ARHGAP10 mutation (deletion/SNV), the present inventors analyzed the influence of the mutation on human neurons. As in the mice, the length of neurites and the number of neurite branches were reduced in human neurons with ARHGAP10 mutation (FIG. 2, panel B).

These findings suggest that mutations in the ARHGAP10 gene identified in patients may be involved in pathogenesis of schizophrenia by causing constant Rho kinase activation. Therefore, the present inventors decided to examine whether an Rho kinase inhibitor is applicable as an antipsychotic drug by using model mice and patient-derived iPS cells.

Stimulants that stimulate dopamine receptors, such as methamphetamine (meth), are known to cause hallucinations and delusional symptoms similar to those of schizophrenia (Lieberman et al., 1987). Further, since antipsychotic drugs generally have effects of blocking dopamine D2 receptors, excess dopamine transmission is considered to be involved in the onset of schizophrenia (Howes et al., 2015). However, since negative symptoms are resistant to conventional antipsychotics and are rarely observed in methamphetamine psychosis induced by methamphetamine or amphetamine, a mechanism different from increased dopamine transmission is suggested to be involved in the onset of negative symptoms. On the other hand, phencyclidine (PCP), which is an N-methyl-D-aspartate (NMDA) receptor antagonist, induces schizophrenia-like positive and negative symptoms and cognitive dysfunction in healthy subjects, and also exacerbates psychiatric symptoms in schizophrenic patients (Javitt, D. C. et al, 1991; Volkow, N. D. et al. 1992). Ketamine, which is an anesthetic agent, also induces schizophrenia-like symptoms in healthy subjects (Krystal et al., 1994). Accordingly, glutamatergic neurotransmission is considered to play an important role in the pathogenesis, pathophysiology, and clinical conditions of schizophrenia (Tamminga et al., 1995). MK-801 is a non-competitive antagonist of the NMDA receptor, which is one of the glutamate receptors. MK-801 has been used as a pharmacological model of schizophrenia because experimental animals treated with MK-801 exhibit behavioral abnormality that resembles positive and negative symptoms of schizophrenia and cognitive dysfunction, such as hyperactivity, social behavior disorder, and cognitive impairment (Neill et al., 2010; Cadinu et al., 2017). In order to develop a method for treating schizophrenia based on ARHGAP10 mutation, which is involved in the onset of mental disorder, the present inventors investigated the effect of an Rho kinase inhibitor, fasudil, on behavioral abnormalities observed in genetic mutant model mice with a patient-type ARHGAP10 mutation (deletion/SNV) and in pharmacological model mice produced by administration of meth and MK-801 based on the dopamine and glutamate hypothesis.

2. Method 2.1. Experimental Animal

Genetically mutant model mice with a patient-type ARHGAP10 mutation were originally created by the TALEN method (data unpublished). For the measurement of blood fasudil and brain fasudil concentrations and creation of pharmacological model mice treated with meth or MK-801, seven-week-old male C57BL/6J slc mice (Japan Slc, Shizuoka, Japan) were used. The animals were kept at room temperature of 23*1° C., humidity of 50±5%, light/dark cycle with a light period of 9:00-21:00, and were allowed free access to water and food.

2.2. Reagent

Fasudil hydrochloride hydrate was provided by Asahi Kasei Pharma Corporation (Tokyo, Japan). Methamphetamine hydrochloride (produced by Sumitomo Dainippon Pharma Co., Ltd., Osaka, Japan) and (+)-MK-801 maleate (Sigma, St. Louis, Mo., USA) were purchased.

Measurement of Fasudil in Blood and Brain 2.3.1. Preparation of Blood Samples

The blood samples obtained were treated with heparin and centrifuged (4° C., 1000×g, 10 min). The supernatant was collected and then centrifuged again (4° C., 2000 rpm, 20 min). The supernatant was stored at −80° C. as a plasma sample. After the plasma sample was thawed at room temperature, 800 µl of 1% formic-acid-methanol solution and 160 µl of an internal standard solution (125 ng/ml 1-(5-isoquinolinesulfonyl)piperazine, dihydrochloride, produced by Sigma-Aldrich) were added to 200 µl of the thawed plasma sample, and the resulting mixture was centrifuged (4° C., 1000×g, 5 min). The supernatant was collected and then subjected to solid-phase extraction using Phree-SPE (Phenomenex, Torrance, Calif., USA). The extract was evaporated to dryness at 40° C. The residue was re-dissolved with pure water and then centrifuged (room temperature, 13000 rpm, 5 min). Using 20 µl of the collected supernatant, the fasudil content of the supernatant was measured using a liquid chromatograph tandem mass spectrometer (LC/MS/MS).

2.3.2. Preparation of Brain Samples

Brains removed from mice were washed with saline, and brain regions except for the cerebellum were stored at −80°

C. 20 µl of a 1% formic acid-methanol solution and 4 µl of an internal standard solution were added to 1 mg of each brain sample, and the brain tissue was pulverized using an ultrasonic homogenizer and centrifuged (4° C., 10000 rpm, 5 min). The supernatant was collected, and then the extract was evaporated to dryness at 40° C. The residue was re-dissolved in pure water and then centrifuged (room temperature, 13000 rpm, 5 min). Using 20 µl of the collected supernatant, the fasudil content of the supernatant was measured using LC/MS/MS.

2.3.3. LC/MS/MS Measurement

An ACQUITY UPLC CSH C18 column (100 mm×2.1 mm, waters, Milford, Mass., USA) was used as a separation column and heated to 35° C. As mobile phases, solvent A (5 mM ammonium acetate aqueous solution) and solvent B (methanol) were used. The conditions were set to % B (5-80/90 sec) at a flow rate of 0.2 ml/min. Samples were ionized by ESI in positive ion mode, and 292.13 m/z→98.706 m/z, 292.13 m/z→98.703 m/z, and 292.13 m/z→69.5 m/z were detected as fasudil by the multiple reaction monitoring measurement method. Based on the obtained peak areas of fasudil and the internal standard substance, the peak area ratio of fasudil to the internal standard substance was calculated. The plasma fasudil concentration and the brain fasudil concentration were calculated using calibration curves. The calibration curve prepared by using a standard solution of fasudil dissolved in fresh human frozen plasma showed a correlation coefficient of 0.99 in the concentration range of 1 to 1000 ng/mL, and a diurnal variation and a day-to-day variation of less than 5%. The calibration curve prepared by using a fasudil standard solution produced from a mouse brain homogenate solution showed a correlation coefficient of 0.99 in the concentration range of 0.03 to 3 ng/brain tissue weight (mg), and a diurnal variation and a day-to-day variation of less than 5%.

2.4. Behavioral Tests 2.4.1. Spontaneous Locomotor Activity

Mice were placed one by one in measurement cages (25 cm×30 cm×18 cm). Immediately after the placement, spontaneous locomotor activity of mice was measured using a measurement device equipped with infrared light (Brain Science Idea, Osaka, Japan) (Ibi et al., 2010).

2.4.2. Visual Discrimination Test

A touchscreen operant device (Phenosys, Berlin, Germany; Brain Science Idea, Osaka, Japan) was used. The front surface of a touch screen monitor (5×4 inches) installed inside the device was equipped with an acrylic plate with two square holes, through which mice could touch the touch screen monitor. The back surface of the touch screen monitor was provided with a water supply nozzle for providing milk as a reward. The mice were allowed to consume food and water only for two hours a day for one week before the start of the behavioral experiment, and food restriction was continued throughout the training period. Mice were trained to obtain food by touching a white square presented on the touch screen. Mice that achieved a correct response rate of 75% or more for two consecutive days were used in the subsequent visual discrimination experiment. In the experiment, a fan-shaped pattern and a ball-shaped pattern were presented simultaneously in the left and right holes of the screen, and a reward was given when one specific pattern was touched, whereas no reward was given when the other pattern was touched. During the test period, the patterns were presented randomly on both sides, and the combination of pattern and reward was fixed. Patterns were presented thirty times in one test. The correct response rate, the test completion rate, the latency to correct response, and the latency to obtain the reward were recorded (Wulaer et al., 2018).

2.4.3 Social Behavior Test

Before conducting the experiment, test mice were kept in breeding cages one by one for 2 days. On the third day, mice that had been normally group-reared in another breeding cage were placed as invading mice into the cages of the test mice, and social behaviors of the test mice, such as tracking and sniffing, were measured for 5 minutes (Ibi et al., 2010).

2.5 Analysis Using iPS Cells 2.5.1 Neuron Induction from iPS Cells

Dopaminergic neurons were induced from iPS cells of healthy subjects and patients with ARGHAP10 mutation. The induction method was performed according to a method already published (Transl Psychiatry. 2018 Jul. 19; 8(1): 129; and patent application PCT/JP2018/015304). To give an overview, iPS cells were cultured in an iPS cell medium supplemented with SB431542 (3 µM), CHIR99021 (3 µM), and dorsomorphin (3 µM) for 7 days (day 0 to day 7). The cultured cells were then dispersed with TrypLE™ select (Thermo Fisher Scientific Inc.) and passed through a cell strainer. The resulting cells were float-cultured for 2 weeks in a neurosphere medium (a medium obtained by preparing a DMEM/F12 medium with 1×N2 supplement, 0.6% glucose, penicillin/streptomycin, and 5 mM HEPES (MHM medium) and adding to this medium 1×B27 supplement, 20 ng/ml bFGF, 10 ng/ml human LIF, 10 µM Y27632, 3 µM CHIR99021, 2 µM SB431542, 100 ng/ml FGF8, and 1 µM plumorphamine). Neurospheres were thereby formed (day 7 to day 21). GF8 and plumorphamine were added from day 10. The neurospheres were collected on day 14, dispersed to form single cells, and then float-cultured again to re-form neurospheres (secondary neurospheres). On day 21, the neurospheres were seeded onto a culture dish coated with Matrigel™ (BD) or with poly-L-ornithine/laminin/fibronectin (poly-L-ornithine, laminin, and fibronectin), and then cultured in a medium for dopamine neurons (an MHM medium with B27 supplement, 10 µM DAPT, 20 ng/ml BDNF, 20 ng/ml GDNF, 0.2 mM ascorbic acid, 1 ng/ml TGF-β3, and 0.5 mM dbcAMP) to induce differentiation into dopamine neutrons (day 21 onward). All cultures were grown in a normal CO; incubator (5% $CO_2$; oxygen concentration: 18.5% to 19.5% (not adjusted)).

2.5.2 Rho Kinase Inhibitors

Fasudil hydrochloride hydrate was provided by Asahi Kasei Pharma (Tokyo, Japan). Y-27632 (produced by Wako Pure Chemical Co., Ltd.) and lipasudil (produced by Selec Chemicals, Inc.) were purchased.

2.5.3 Measurement of Neurite Length

Dopaminergic progenitor cells were seeded onto a culture dish coated with poly-L-ornithine/laminin/fibronectin (poly-L-ornithine, laminin, and fibronectin), and an Rho kinase inhibitor was added simultaneously. For the control (=0 µM), water, which was used as a solvent of the inhibitor, was added. The length of neurites after 72 hours was automatically measured with IncuCyte NeuroTrack (registered trademark).

3. Results and Discussion 3.1 Plasma Fasudil and Brain Fasudil Concentrations

Figure 3:
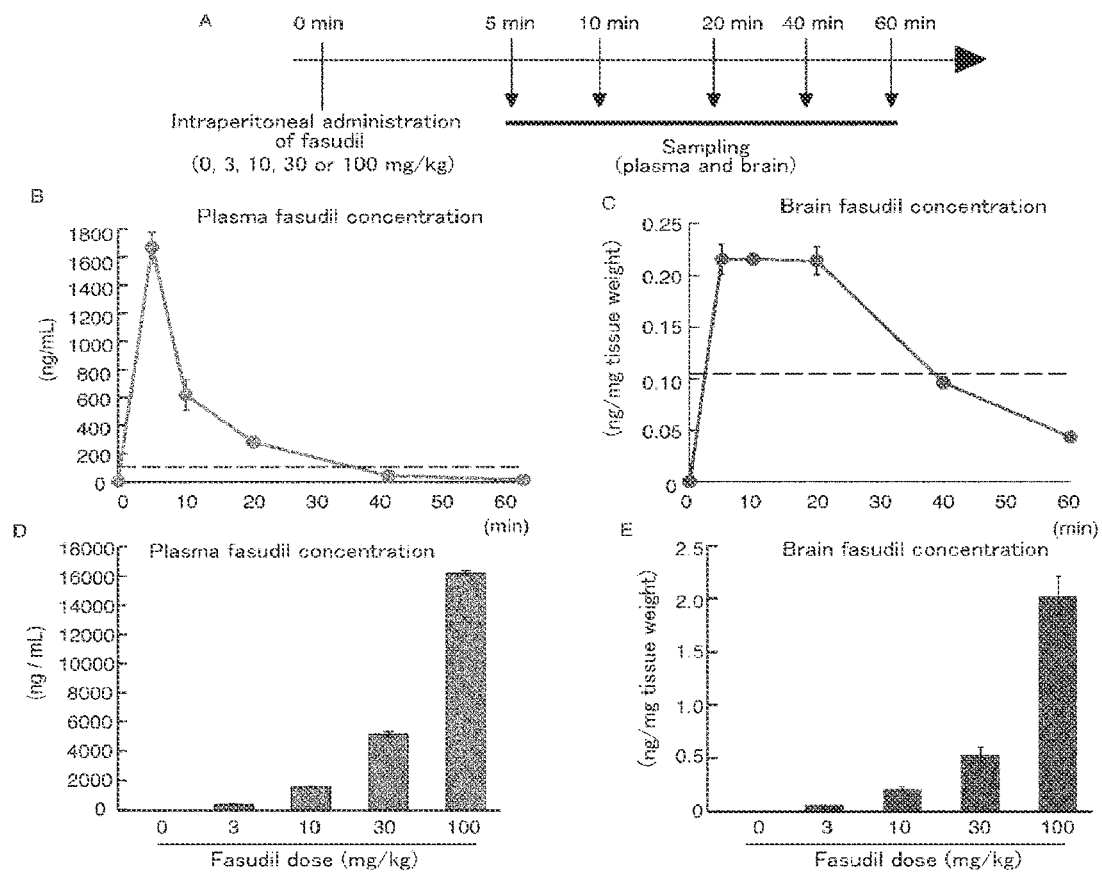
FIG. 3 shows an experimental scheme (A) and plasma fasudil concentrations (B) and (D) and brain fasudil concentrations (C) and (E).

In accordance with the experimental schedule shown in FIG. 3, panel A, fasudil was intraperitoneally administered into C57BL/6 mice, and plasma and brain samples were collected. The plasma fasudil concentration in C57BL/6 mice intraperitoneally injected with 10 mg/kg fasudil reached the highest value of about 1600 ng/ml 5 minutes after the administration and then decreased (FIG. 3, panel B). The blood fasudil concentrations 5, 10 and 20 minutes after the administration were higher than the Ki value of fasudil for Rho-kinase of 104 ng/ml. The brain fasudil concentration showed a high value of about 0.2 ng/mg tissue during a period from 5 to 20 minutes after the administration, and then decreased to the Ki value of fasudil for Rho kinase of 0.104 ng/mg tissue 40 minutes after the administration of fasudil (FIG. 3, panel C). The plasma fasudil and brain fasudil concentrations 5 minutes after the administration of fasudil showed an increase in a dose-dependent manner, and the plasma fasudil concentration was higher than the Ki value of fasudil for Rho kinase at a dose of 3 mg/kg or more, whereas the brain fasudil concentration was higher than the Ki value of fasudil for Rho kinase at a dose of 10 mg/kg or more (FIG. 3, panels D and E). These results suggest that when fasudil is intraperitoneally administered at a dose of 10 mg/kg or more, fasudil is present in the brain at a concentration that sufficiently inhibits Rho kinase during a period from 5 to 40 minutes after administration.

3.2 Effect of Fasudil on Spontaneous Locomotor Activity

Figure 4:
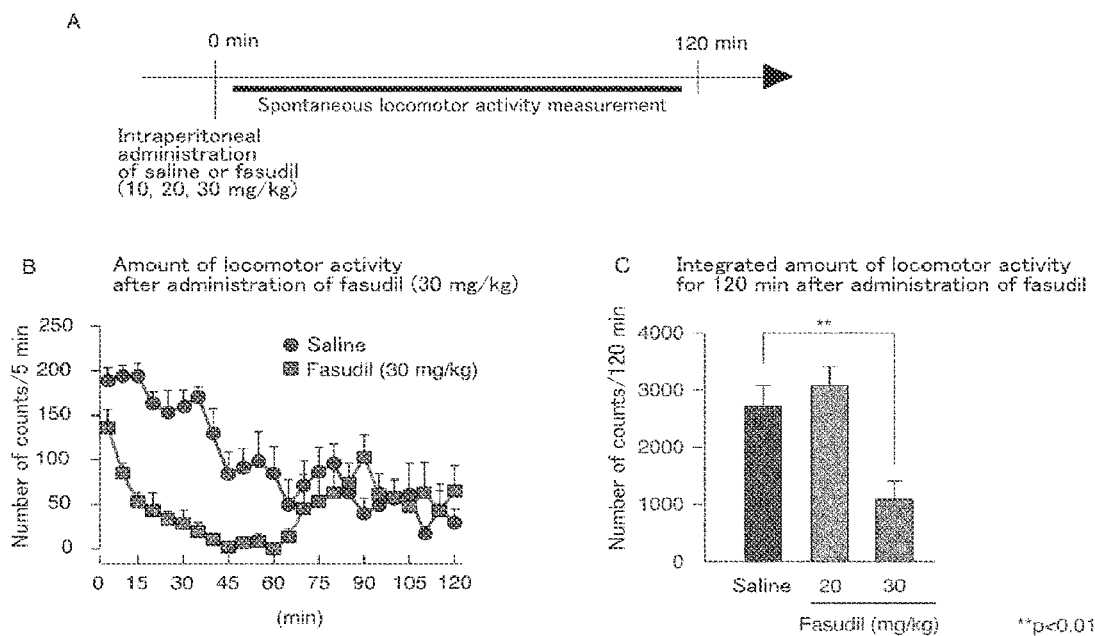
FIG. 4 shows an experimental scheme (A) and effects of fasudil on spontaneous locomotor activity (B)-(C).

Saline or fasudil (20 or 30 mg/kg) was intraperitoneally administered to C57BL/6 mice, and spontaneous locomotor activity of the mice started to be measured immediately after the administration (FIG. 4, panel A). As compared with the saline-treated mice, the mice treated with 30 mg/kg of fasudil had a significant decrease in spontaneous locomotor activity immediately after the administration (FIG. 4, panel B). On the other hand, the mice treated with 20 mg/kg of fasudil showed the same level of spontaneous locomotor activity as the saline-treated mice (FIG. 4, panel C). These results suggest that administration of more than 30 mg/kg of fasudil to mice impairs locomotor function.

Figure 5:
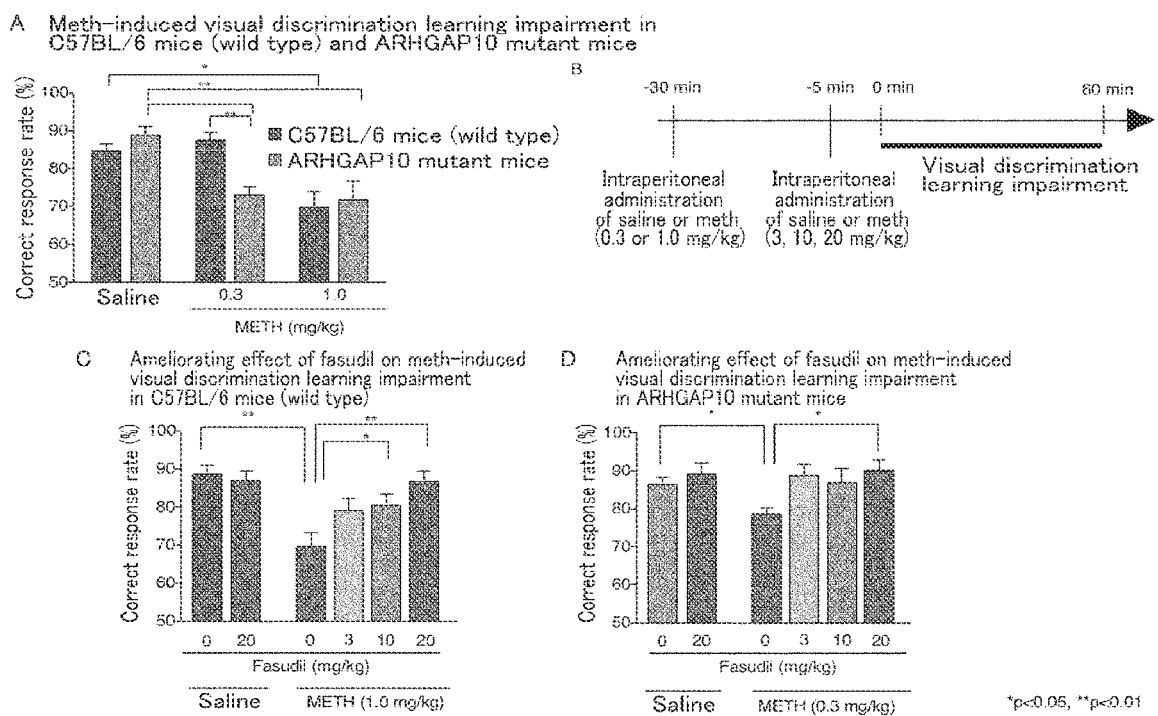
FIG. 5 shows meth-induced visual discrimination learning impairment in C57BL/6 mice (wild type) and ARHGAP10 mutant mice (A), and experimental scheme (B), and ameliorating effects of fasudil (C)-(D).

3.3. Meth-Induced Visual Discrimination Learning Impairment in C57BL/6 Mice (Wild Type) and ARHGAP10 Mutant Mice and Ameliorating Effect of Fasudil A research group of the present inventors previously found that C57BL/6 mice (wild type) to which meth was administered in an amount of 1.0 mg/kg 30 minutes before the test had visual discrimination learning impairment (FIG. 5, panel A). The present inventors also found that in ARHGAP10 mutant mice, meth-induced visual discrimination learning impairment was induced by a lower dose of meth (0.3 mg/kg) (FIG. 3, panel A). Accordingly, the present inventors investigated ameliorating effects of fasudil on meth-induced visual discrimination learning impairment observed in both mice (FIG. 5, panel B). The saline-treated C57BL/6 mice had a correct response rate of about 90% in the visual discrimination learning test, whereas the 1.0 mg/kg meth-treated mice had a correct response rate of about 70%, thus indicating learning impairment. The meth-induced visual discrimination learning impairment observed in C57BL/6 mice was improved by administration of fasudil (10 mg/kg or 20 mg/kg) to the mice (FIG. 5, panel C). Fasudil (20 mg/kg) also significantly improved the meth-induced visual discrimination learning impairment observed in ARHGAP10 mutant mice (FIG. 5, panel D). These results show that fasudil ameliorates the cognitive dysfunction exhibited by genetic animal models with ARHGAP10 genomic mutation and in pharmacological animal models using meth.

3.4. Inhibitory Effect of Fasdil on Hyperactivity in MK-801-Treated Mice

Figure 6:
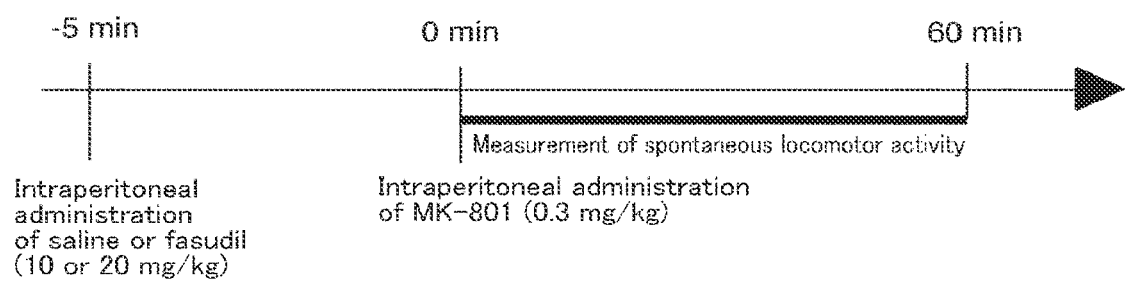
FIG. 6 shows an experimental scheme (A) and inhibitory effects of fasudil on hypermobility in MK-801-treated mice (B).
Figure 6:
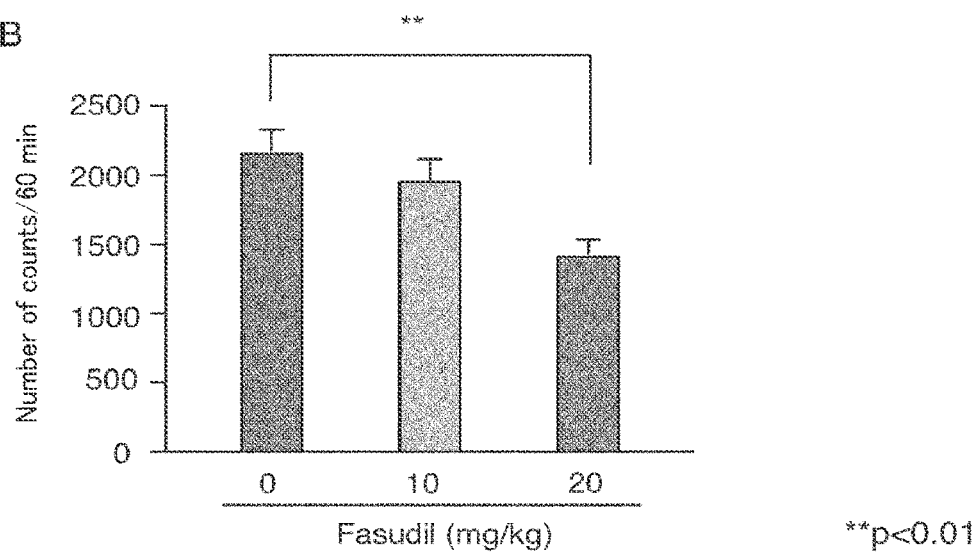

Saline or fasudil (10 or 20 mg/kg) was intraperitoneally administered to C57BL/6 mice. After 5 minutes, MK-801 (0.3 mg/kg) was intraperitoneally administered. The amount of locomotor activity started to be measured immediately after the administration (FIG. 6, panel A). MK-801-induced hyperactivity was significantly inhibited in mice treated with fasudil (20 mg/kg) (FIG. 6, panel B). Accordingly, fasudil can be thought to inhibit psychomotor excitation in animal models using MK-801.

Figure 7:
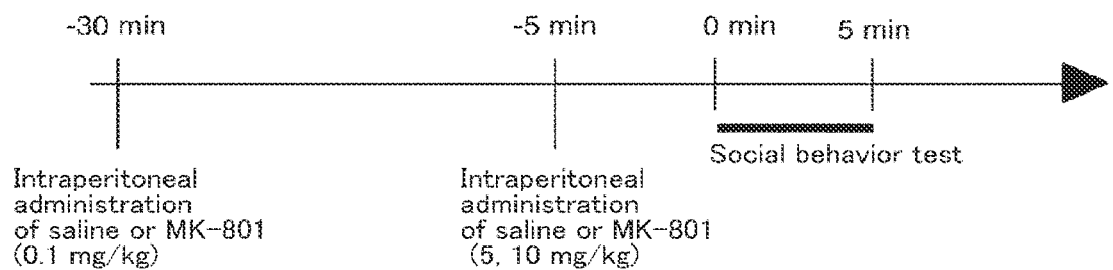
FIG. 7 shows an experimental scheme (A) and ameliorating effects of fasudil on social behavior disorder in MK-801-treated mice (B).
Figure 7:
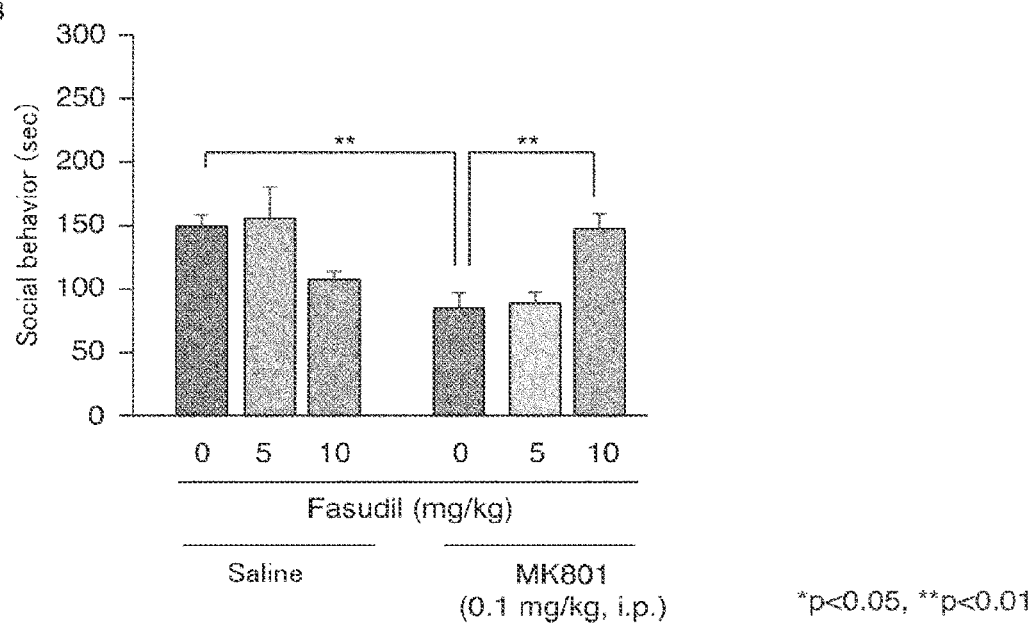

Ameliorating Effect of Fasudil on Social Behavior Disorder in MK-801-Treated Mice Saline or MK-801 (0.1 mg/kg) was intraperitoneally administered to C57BL/6 mice 30 minutes before the start of the experiment. Five minutes before the start of the experiment, saline or fasudil (5 or 10 mg/kg) was intraperitoneally administered, and social behavior was measured. (FIG. 7, panel A). The time of social behavior disorder was significantly reduced in the MK-801-treated mice, as compared with the control mice (FIG. 7, panel B). The impaired social behavior observed in MK-801-treated mice returned to the same level as the social behavior in control mice by administration of fasudil (10 mg/kg) (FIG. 7, panel B). These results show that fasudil has an ameliorating effect on social behavior disorders present in MK-801-treated animal models.

Figure 8:
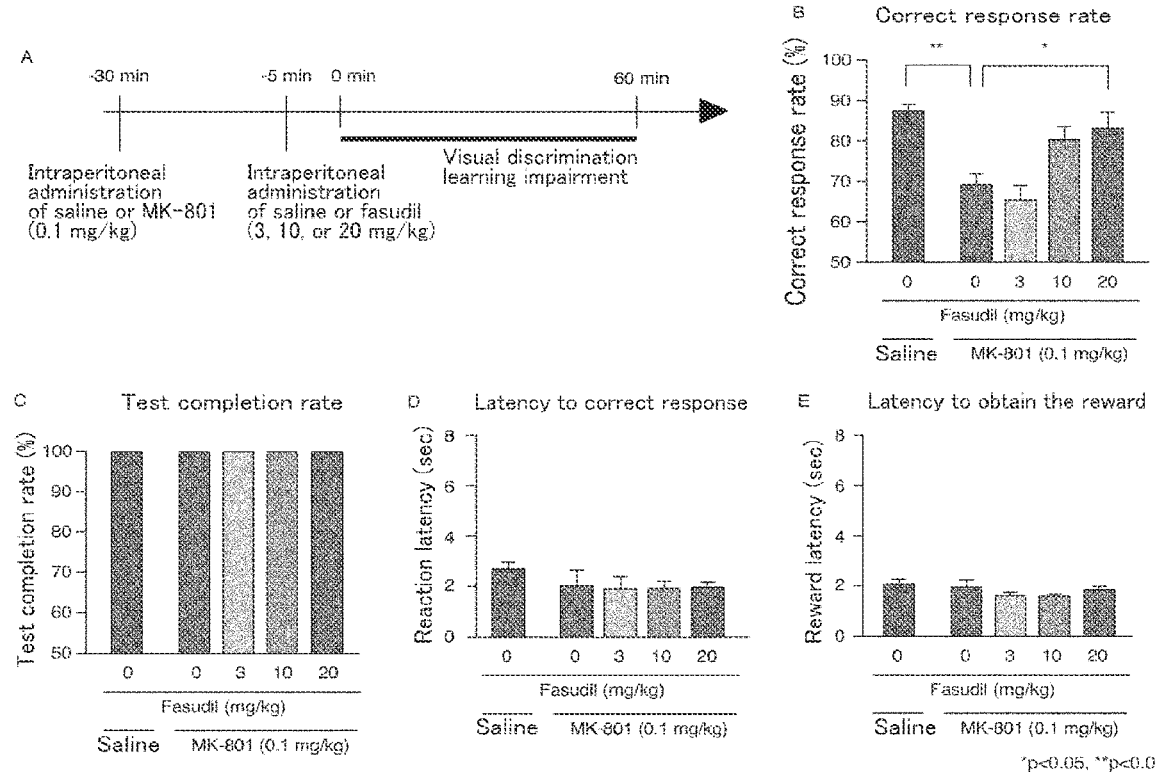
FIG. 8 shows an experimental scheme (A) and ameliorating effects of fasudil on visual discrimination learning impairment in MK-801-treated mice (B)-(E).

3.6. Ameliorating Effect of Fasudil on Visual Discrimination Learning Impairment in MK-801-Treated Mice Saline or MK-801 (0.1 mg/kg) was intraperitoneally administered to C57BL/6 mice 30 minutes before the start of the experiment. 5 minutes before the start of the experiment, saline or fasudil (3, 10, or 20 mg/kg) was intraperitoneally administered to the C57BL/6 mice, and a visual discrimination test was performed (FIG. 8, panel A). The saline-treated C57BL/6 mice had a correct response rate of 90% in the visual discrimination learning test, whereas the MK-801-treated mice had a correct response rate of about 70%, thus indicating learning impairment (FIG. 8, panel B). The MK-801-induced visual discrimination learning impairment observed in the C57BL/6 mice returned to the control level by administration of fasudil (20 mg/kg) (FIG. 8, panel B). In this test, none of the groups showed significant changes in correct response rate, test completion rate, latency to correct response, or latency to obtain the reward (FIG. 8, panels C to E). Accordingly, fasudil was shown to improve cognitive dysfunction exhibited by the MK-801 animal model without producing adverse effects on attention or motivation.

3.7. Rho Kinase Inhibitor Addition Experiment Using Human iPS Cells

Figure 9:
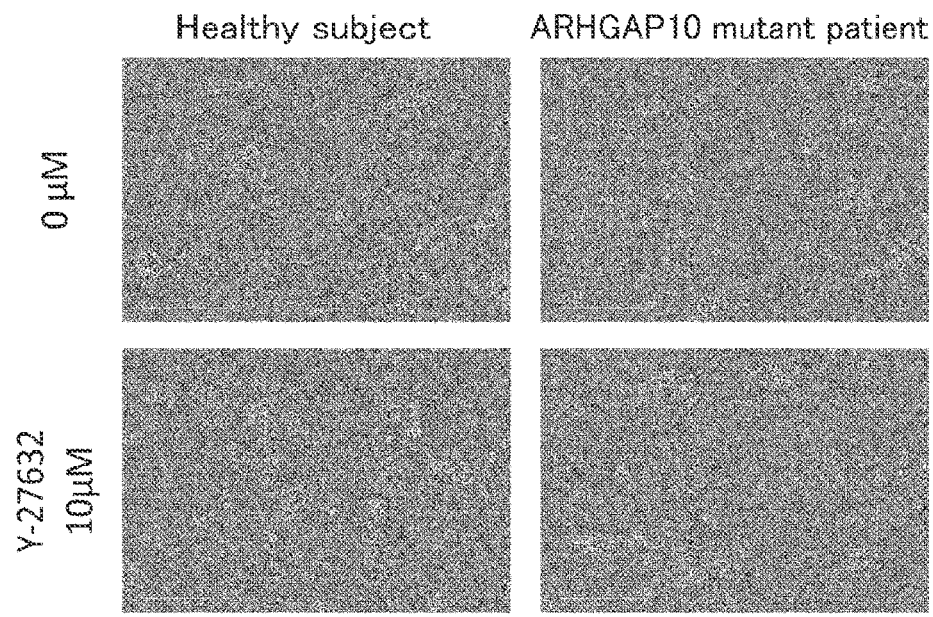
FIG. 9 shows examples of automated detection of neurites.

Dopaminergic neurons were induced from iPS cells derived from healthy subjects and patients with ARHGAP10 mutation. The effects of Rho kinase inhibitors (fasudil, repasudil, Y-27632) were examined. The length of neurites was used as an index of evaluation. The length of neurites was automatically detected and measured with IncuCyte (registered trademark) NeuroTrack (produced by Essen Bioscience). FIG. 9 shows examples of neurite detection.

Figure 10:
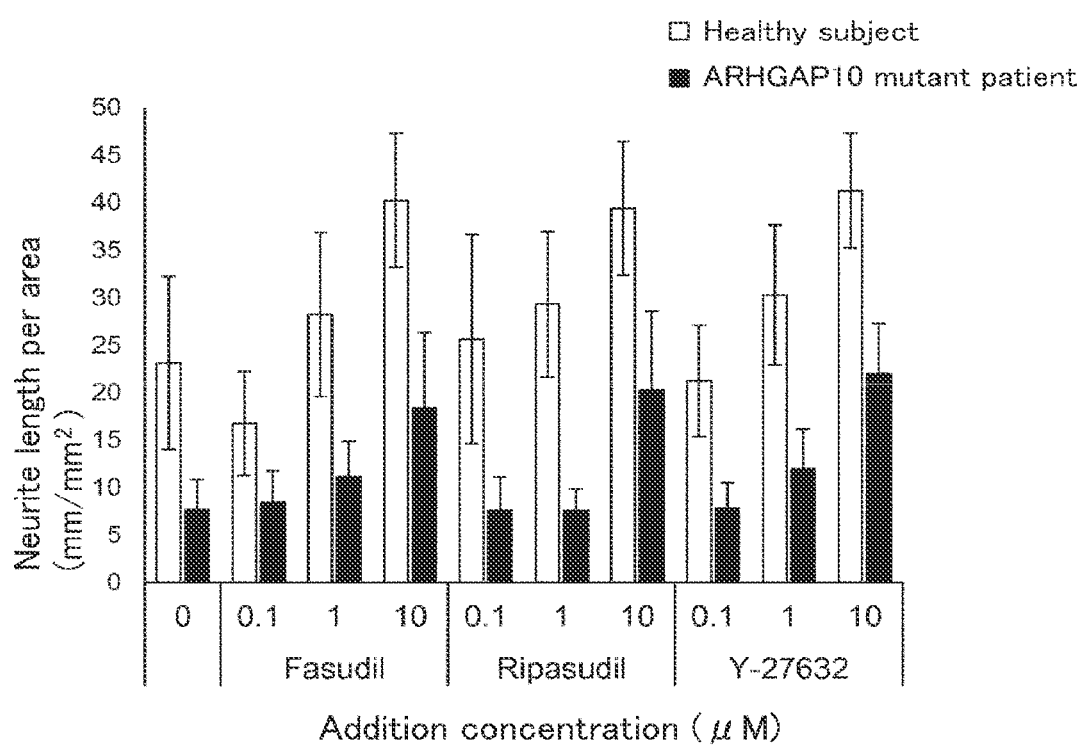
FIG. 10 shows examination of effects of Rho kinase inhibitors using human iPS cell-derived neurons.

The length of neurites (mm) per $mm^2$ was calculated for each field of view, and analysis was performed for 18 fields of view in each group. The length of neurites in neurons of the ARHGAP10 patients was shorter than in the healthy subjects. However, the addition of each Rho kinase inhibitor tended to improve the length of neurites in a concentration-dependent manner (FIG. 10; the graph shows mean±SD).

4. Summary

Table 1 shows the results obtained in this study. These results clearly show that the Rho kinase inhibitor fasudil has an ameliorating effect on abnormal behaviors observed in the gene mutation models with a patient-type ARHGAP10 mutation (deletion/SNV), dopamine hypothesis models, and glutamate hypothesis models. Also observed were improving effects (improvement in protrusion length) of three types of Rho kinase inhibitors, including fasudil, on neurons derived from patient iPS cells.

The above suggests that the Rho kinase inhibitors can be useful as novel therapeutic agents based on the pathology of schizophrenia. Further, in view of the fact that the same genome mutation (especially a neurodevelopment-related gene) is a risk for not only schizophrenia, but also autism spectrum disorder and bipolar disorder, and that existing antipsychotic drugs for schizophrenia are also used for the treatment of autism spectrum disorder, bipolar disorder, and depression, Rho kinase inhibitors are expected to be useful as therapeutic agents not only for schizophrenia but also for autism spectrum disorder, bipolar disorder, and depression, which are associated with neurodevelopment.

TABLE 1

Antipsychotic effect of Fasudil

| Animal model | Behavioral test | Fasudil dose (mg/kg, intraperitoneal administration) | | | | |
| --- | --- | --- | --- | --- | --- | --- |
| | | 3 | 5 | 10 | 20 | 30 |
| Patient-type ARHGAP mutant mice (genetic mutation model) | Meth-induced (0.3 mg/kg) visual discrimination impairment | Improved | N.D. | Improved | Improved | N.D. |
| Meth-treated mice (dopamine hypothesis model) | Math induced (1.0 mg/kg) visual discrimination impairment | Improvement tendency | N.D. | Improved | Improved | N.D. |
| MK-801 treated mice (glutamate hypothesis model) | Spontaneous locomotor activity | N.D. | N.D. | N.D. | ± | Decreased |
| | MK-801-induced hypermobility | N.D. | N.D. | ± | Improved | N.D. |
| | MK-801-induced social behavior disorder | N.D. | ± | Improved | ± | N.D. |
| | MK-801-induced (1.0 mg/kg) visual discrimination disorder | ± | N.D. | Tendency of improvement | Improved | N.D. |

N.D.: No data
±: No change

REFERENCES

Cadinu D. et al., NMDA receptor antagonist rodent models for cognition in schizophrenia and identification of novel drug treatments, an update. Neuropharmacology pii: 50028-3908(17)30584-1, 2017.

Howes O., McCutcheon R, Stone J., Glutamate and dopamine in schizophrenia: an update for the 21st century. J Psychopharmacol 29:97-115, 2015.

Ibi D. et al., Combined effect of neonatal immune activation and mutant DISC1 on phenotypic changes in adulthood. Behav Brain Res 206:32-37, 2010.

Javitt D. C. et al., Recent advances in the phencyclidine model of schizophrenia. Am J Psychiatry 148: 1301-1308, 1991.

Krystal J. H. et al., Subanesthetic effects of the noncompetitive NMDA antagonist, ketamine, in humans. Psychotomimetic, perceptual, cognitive, and neuroendocrine responses. Arch Gen Psychiatry 51:199-214, 1994.

Kushima I. et al., High-resolution copy number variation analysis of schizophrenia in Japan. Mol Psychiatry 22:430-440, 2017.

Lieberman J. A., Kane J. M., Alvir J., Provocative tests with psychostimulant drugs in schizophrenia. Psychopharmacology 91:415-33, 1987.

Neill J. C. et al., Animal models of cognitive dysfunction and negative symptoms of schizophrenia: Focus on NMDA receptor antagonism. Pharmacol Ther 128:419-432, 2010.

Tamminga C. A. et al., Glutamate pharmacology and the treatment of schizophrenia: current status and future directions. Int Clin Psychopharmacol 10:29-37, 1995.

Volkow N. D. et al., Neuropsychiatric disorders: investigation of schizophrenia and substance abuse. Semin Nucl Med 22:254-267, 1992.

Wulaer B. et al., Repetitive and compulsive-like behaviors lead to cognitive dysfunction in Disc1$^{\Delta 2-3/\Delta 2-3}$ mice. Genes Brain Behav April 10: e12478, 2018.

INDUSTRIAL APPLICABILITY

The antipsychotic drug of the present invention can be used as a pathology-based treatment agent for various mental disorders with abnormal neurodevelopment as a pathological condition. That is, since the present invention can be applied to the treatment of schizophrenia as well as the treatment of autism spectrum disorder, bipolar disorder, depression, etc., its utility value and clinical significance is extremely great.

The present invention is not limited in any way to the above explanation of the embodiments or the examples of the present invention. Various modifications easily conceivable by a person skilled in the art without departing from the scope of the claims also fall within the scope of the present invention. The entire contents of the literature, laid-open patent publications, patent gazettes, and the like specified in the present specification are incorporated herein by reference.

The invention claimed is:

1. A method for the treatment of schizophrenia in a patient in need thereof, wherein the method comprises administering to the patient a therapeutically effective amount of fasudil, or a pharmacologically acceptable salt or hydrate thereof.

2. The method according to claim 1, wherein the fasudil, or the pharmacologically acceptable salt or hydrate thereof, is hexahydro-1-(5-isoquinolinesulfonyl)-1H-1,4-diazepine monohydrochloride hemihydrate.

3. The method according to claim 1, wherein the method comprises administering to the patient once to several times a day a therapeutically effective amount of the fasudil, or the pharmacologically acceptable salt or hydrate thereof.

4. The method according to claim 1, wherein the method comprises administering to the patient once every two days a therapeutically effective amount of the fasudil, or the pharmacologically acceptable salt or hydrate thereof.

5. The method according to claim 1, wherein the method comprises administering to the patient once every three days a therapeutically effective amount of the fasudil, or the pharmacologically acceptable salt or hydrate thereof.

6. The method according to claim 1, wherein the method comprises orally administering to the patient a therapeutically effective amount of the fasudil, or the pharmacologically acceptable salt or hydrate thereof.

7. The method according to claim 1, wherein the method comprises administering to the patient a therapeutically effective amount of the fasudil, or the pharmacologically acceptable salt or hydrate thereof, in combination with one or more additional active ingredients selected from the group consisting of aripiprazole, asenapine, blonanserin, bromperidol, carpipramine, chlorpromazine, clocapramine, clozapine, fluphenazine, haloperidol, levomepromazine, moperone, mosapramine, nemonapride, olanzapine, paliperidone, perospirone, perphenazine, pimozide, propericiazine, quetiapine, risperidone, spiperone, sulpiride, sultopride, tiapride, and zolpidem.

8. The method according to claim 1, wherein the schizophrenia is associated with dysfunction of ARHGAP10.

9. The method according to claim 8, wherein the dysfunction of ARHGAP10 is a deletion in the ARHGAP10 gene or a deletion of the ARHGAP10 gene.

10. The method according to claim 8, wherein the dysfunction of ARHGAP10 is an amino acid substitution of proline for serine at residue 490 (Ser490Pro).

11. The method according to claim 8, wherein the fasudil, or the pharmacologically acceptable salt or hydrate thereof, normalizes dysfunction of ARHGAP10.

12. The method according to claim 8, wherein the fasudil, or the pharmacologically acceptable salt or hydrate thereof, is hexahydro-1-(5-isoquinolinesulfonyl)-1H-1,4-diazepine monohydrochloride hemihydrate.

13. The method according to claim 8, wherein the method comprises administering to the patient once to several times a day a therapeutically effective amount of the fasudil, or the pharmacologically acceptable salt or hydrate thereof.

14. The method according to claim 8, wherein the method comprises administering to the patient once every two days a therapeutically effective amount of the fasudil, or the pharmacologically acceptable salt or hydrate thereof.

15. The method according to claim 8, wherein the method comprises administering to the patient once every three days a therapeutically effective amount of the fasudil, or the pharmacologically acceptable salt or hydrate thereof.

16. The method according to claim 8, wherein the method comprises orally administering to the patient a therapeutically effective amount of the fasudil, or the pharmacologically acceptable salt or hydrate thereof.

17. The method according to claim 8, wherein the method comprises administering to the patient a therapeutically effective amount of the fasudil, or the pharmacologically acceptable salt or hydrate thereof, in combination with one or more additional active ingredients selected from the group consisting of aripiprazole, asenapine, blonanserin, bromperidol, carpipramine, chlorpromazine, clocapramine, clozapine, fluphenazine, haloperidol, levomepromazine, moperone, mosapramine, nemonapride, olanzapine, paliperidone, perospirone, perphenazine, pimozide, propericiazine, quetiapine, risperidone, spiperone, sulpiride, sultopride, tiapride, and zolpidem.

\* \* \* \* \*